US011638576B2

(12) United States Patent
Groenland et al.

(10) Patent No.: US 11,638,576 B2
(45) Date of Patent: May 2, 2023

(54) WIRELESS INTRALUMINAL IMAGING DEVICE AND ASSOCIATED DEVICES, SYSTEMS, AND METHODS

(71) Applicant: KONINKLIJKE PHILIPS N.V., Eindhoven (NL)

(72) Inventors: Alfons Wouter Groenland, Best (NL); Arjen van der Horst, Tilburg (NL); Derk Reefman, Best (NL); David Holt Burkett, Panama City Beach, CA (US); Cesar Perez, Roseville, CA (US); Joseph James Hoffman, Sacramento, CA (US); Gerald Litzza, Rancho Cordova, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 214 days.

(21) Appl. No.: 16/348,548

(22) PCT Filed: Nov. 7, 2017

(86) PCT No.: PCT/EP2017/078374
§ 371 (c)(1),
(2) Date: May 9, 2019

(87) PCT Pub. No.: WO2018/087050
PCT Pub. Date: May 17, 2018

(65) Prior Publication Data
US 2019/0261958 A1 Aug. 29, 2019

Related U.S. Application Data

(60) Provisional application No. 62/420,766, filed on Nov. 11, 2016.

(51) Int. Cl.
*A61B 8/00* (2006.01)
*A61B 8/12* (2006.01)
*A61B 8/14* (2006.01)

(52) U.S. Cl.
CPC .................. *A61B 8/56* (2013.01); *A61B 8/12* (2013.01); *A61B 8/14* (2013.01); *A61B 8/445* (2013.01); *A61B 8/4488* (2013.01)

(58) Field of Classification Search
CPC .... A61B 8/56; A61B 8/12; A61B 8/14; A61B 8/445; A61B 8/4488
See application file for complete search history.

(56) References Cited

U.S. PATENT DOCUMENTS 6,233,490 B1 * 5/2001 Kasevich ............... A61B 18/18
606/33
6,275,738 B1 * 8/2001 Kasevich ............... A61B 18/18
607/101

(Continued)

FOREIGN PATENT DOCUMENTS

WO 2010020939 A2 2/2010
WO WO-2010020939 A2 * 2/2010 ......... G01S 15/8915

OTHER PUBLICATIONS

International Search Report and Written Opinion for International Application No. PCT/EP2017/078374, filed Nov. 7, 2017, 12 pages.

*Primary Examiner* — Joseph M Santos Rodriguez
*Assistant Examiner* — Kaitlyn E Sebastian

(57) ABSTRACT

A wireless intraluminal imaging device and an associated system are provided. In one embodiment, the wireless intraluminal imaging device includes a flexible elongate member including a proximal portion and a distal portion; an ultrasound imaging component coupled to the distal portion of the flexible elongate member; a cable coupled to the ultrasound imaging component and extending along the flexible elongate member; and a wireless communication (Continued)

component coupled to the proximal portion of the flexible elongate member, the wireless communication component in communication with the ultrasound imaging component via the cable. The wireless communication component wirelessly transmits ultrasound echo signals collected by the ultrasound imaging component to an image processing system via a wireless link for image generation at the image processing component.

21 Claims, 8 Drawing Sheets

(56) References Cited

U.S. PATENT DOCUMENTS

| | | | |
|---|---|---|---|
| 2005/0228370 A1* | 10/2005 | Sterzer | A61B 18/18 606/33 |
| 2006/0211945 A1* | 9/2006 | Mauge | A61B 5/031 600/488 |
| 2006/0270915 A1* | 11/2006 | Ritter | A61B 34/73 600/300 |
| 2008/0110261 A1* | 5/2008 | Randall | G01S 7/5208 73/592 |
| 2008/0300027 A1* | 12/2008 | Dou | H03G 3/3042 455/574 |
| 2009/0105597 A1* | 4/2009 | Abraham | A61B 8/08 600/466 |
| 2010/0130880 A1* | 5/2010 | Li | A61B 5/0086 600/504 |
| 2010/0234736 A1 | 9/2010 | Corl | |
| 2014/0276074 A1* | 9/2014 | Warner | D07B 1/0693 600/459 |
| 2015/0245816 A1* | 9/2015 | Poland | A61B 8/54 600/447 |
| 2015/0289749 A1* | 10/2015 | Stigall | A61B 8/12 600/427 |
| 2016/0029995 A1* | 2/2016 | Navratil | A61B 5/08 600/301 |
| 2016/0170618 A1* | 6/2016 | Song | G06F 3/04883 600/443 |

* cited by examiner

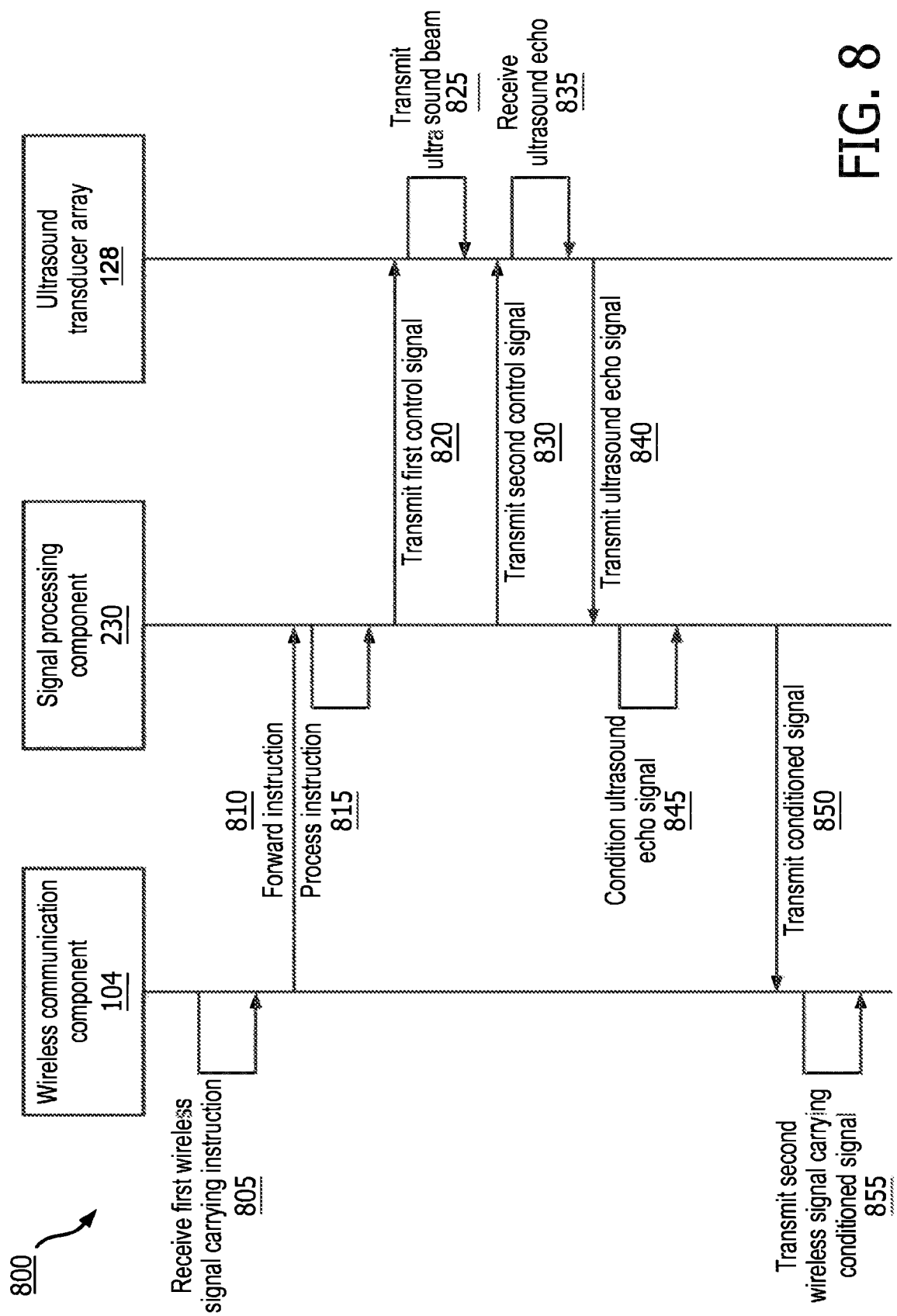

WIRELESS INTRALUMINAL IMAGING DEVICE AND ASSOCIATED DEVICES, SYSTEMS, AND METHODS

RELATED APPLICATIONS

This application is the U.S. National Phase application under 35 U.S.C. § 371 of International Application No. PCT/EP2017/078374, filed on Nov. 7, 2017, which claims the benefit of and priority to U.S. Provisional Ser. No. 62/420,766, filed Nov. 11, 2016, which is incorporated by reference in its entirety.

TECHNICAL FIELD

The present disclosure relates generally to intraluminal imaging and, in particular, to providing wireless communication between an intraluminal imaging device and a processing system for display and control.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed. IVUS imaging can provide detailed and accurate measurements of lumen and vessel sizes, plaque areas and volumes, and location of key anatomical landmarks. IVUS imaging allows physicians to evaluate the size of a lesion, select a treatment device (e.g., a stent) based on the evaluated lesion size, and subsequently evaluate the treatment success.

There are two types of IVUS catheters commonly in use today: rotational and solid-state. For a typical rotational IVUS catheter, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

Solid-state IVUS catheters carry an ultrasound imaging assembly that includes an array of ultrasound transducers distributed around its circumference along with one or more integrated circuit controller chips mounted adjacent to the transducer array. The solid-state IVUS catheters are also referred to as phased array IVUS transducers or phased array IVUS devices. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

In operation, an IVUS device may be connected to a number of cables, for example, a power cable and a communication cable. The IVUS device may receive power from the power cable for operating an ultrasound imaging assembly included in the IVUS device. The IVUS device may communicate with a console or processing system over the communication cable for controlling the operations of the ultrasound imaging assembly and reading out measurements (e.g., ultrasound echo signals) collected by the ultrasound imaging assembly for image analysis and display.

IVUS procedures are typically performed in a catheter lab. The use of the IVUS device in the catheter lab increases the number of cables in the catheter lab and may clutter the workspace of the catheter lab. In addition, sterilization is important when operating in a catheter lab. The connecting and/or disconnecting of an unsterile console or processing system to a sterile IVUS device may be an issue in the catheter lab. One approach is to use detachable cables for connecting IVUS devices to console and processing system. However, detachable cables may not be practical due to the high contact count required for operating the IVUS devices and the high quality or noise sensitivity of ultrasound signals required of IVUS imaging.

SUMMARY

Embodiments of the present disclosure provide a wireless intraluminal imaging system including a catheter fitted with an ultrasound imaging assembly at a distal portion of the catheter and a wireless transceiver and antenna fitted at a proximal portion of the catheter.

In one embodiment, a wireless intraluminal imaging device is provided. The wireless intraluminal imaging device includes a flexible elongate member including a proximal portion and a distal portion; an ultrasound imaging component coupled to the distal portion of the flexible elongate member; a cable coupled to the ultrasound imaging component and extending along the flexible elongate member; and a wireless communication component coupled to the proximal portion of the flexible elongate member, the wireless communication component in communication with the ultrasound imaging component via the cable.

In some embodiments, the wireless communication component includes a transceiver coupled to the cable; and an antenna coupled to the transceiver. In some embodiments, the wireless intraluminal imaging device further comprising a handle coupled to a proximal end of the proximal portion of the flexible elongate member, wherein the handle includes a power source coupled to the cable, and wherein the power source powers the ultrasound imaging component and the wireless communication component via the cable. In some embodiments, the transceiver and the antenna are positioned within the handle. In some embodiments, the transceiver is positioned within the handle, and wherein the antenna extends distally from the transceiver along the proximal portion of the flexible elongate member. In some embodiments, the antenna extends within the flexible elongate member for a first length and along an outer surface of the flexible elongate member for a second length. In some embodiments, the transceiver is positioned within the flexible elongate member adjacent to the handle, and wherein the antenna extends distally from the transceiver and along an outer surface of the flexible elongate member. In some embodiments, the wireless intraluminal imaging device further includes a signal processing component positioned within the handle and in communication with the ultrasound imaging component and the transceiver. In some embodiments, the power source provides power to the signal processing component. In some embodiments, the signal processing component controls transmission and reception by the ultrasound imaging component and conditions ultrasound echo signals collected by the ultrasound imaging component. In some embodiments, the signal processing component conditions the ultrasound echo signals by performing at least one of a filtering, amplifying, aggregating, or compressing of the ultrasound echo signals. In some embodiments, the transceiver receives the conditioned ultrasound echo signals from the signal processing component and wirelessly transmits the conditioned ultrasound echo signals via the antenna. In some embodiments, the transceiver wirelessly receives an instruction via the antenna and transmits the instruction to the signal processing component, and wherein the signal processing component controls at least one of the transmission or the reception of the ultrasound imaging component based on at least the instruction. In some embodiments, the wireless communication component transmits and receives wireless signals at a data rate of at least 1 gigabits per second. In some embodiments, the wireless communication component wirelessly transmits and receives signals at a frequency greater than about 60 gigahertz. In some embodiments, the ultrasound imaging component includes an ultrasound transducer array.

In one embodiment, a wireless intraluminal imaging system includes an intraluminal imaging device including a flexible elongate member including a proximal portion and a distal portion; an ultrasound imaging component coupled to the distal portion of the flexible elongate member; a cable coupled to the ultrasound imaging component and extending along the flexible elongate member; and a first wireless communication component coupled to the proximal portion of the flexible elongate member, wherein the first wireless communication component is in communication with the ultrasound imaging component via the cable; a second wireless communication component in communication with the first wireless communication component of the intraluminal imaging device via a wireless link; and an image processing component in communication with the second wireless communication component, wherein the first wireless communication component wirelessly transmits, to the second wireless communication component via the wireless link, echo data associated with ultrasound echo signals collected by the ultrasound imaging component for image generation at the image processing component.

In some embodiments, the wireless intraluminal imaging system further includes a display component in communication with the image processing component, wherein the image processing component generates an image based on the echo data, and wherein the display component displays the image. In some embodiments, the second wireless communication component wirelessly transmits, to the first wireless communication component via the wireless link, an instruction for controlling ultrasound signal generation at the ultrasound imaging component.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 8 is a signaling diagram of a method of signal transfer in a wireless intraluminal imaging device, according to aspects of the present disclosure.

DETAILED DESCRIPTION

Figure 1:
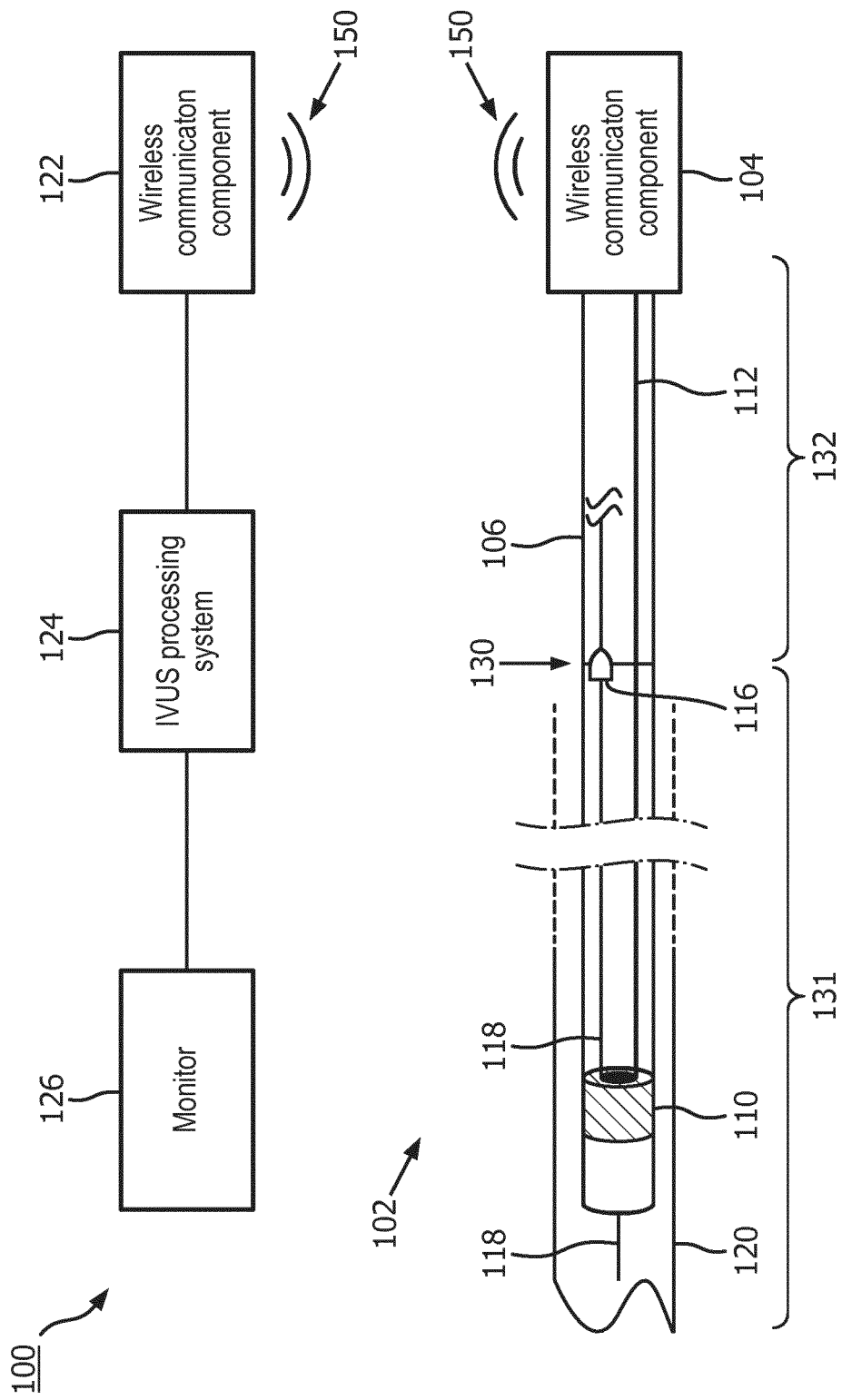
FIG. 1 is a schematic diagram of a wireless intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Disclosed herein are various embodiments of providing a wireless intraluminal imaging device, including a catheter fitted with a wireless communication component. The catheter includes an ultrasound imaging assembly coupled to a distal portion of the catheter and a communication cable coupled to the ultrasound imaging assembly and extending along the catheter. The wireless communication component is coupled to a proximal portion of the catheter and in communication with the ultrasound imaging component via the communication cable. The wireless communication component can wirelessly receive instructions for operating the ultrasound imaging assembly. The wireless communication component can wirelessly transmit ultrasound echo signals collected by the ultrasound imaging assembly for analysis, interpretation, and image generation at a processing system. The wireless communication component includes a wireless transceiver and an antenna, which may be positioned in various configurations at the proximal portion. Although the disclosed embodiments are described in the context of ultrasound imaging, the disclosed embodiments are suitable for use in any other medical imaging or sensing applications.

The disclosed embodiments may provide several benefits over wired intraluminal imaging devices. For example, the use of wireless intraluminal imaging devices reduces the number of cables required in a catheter lab, and thus reduces cluttering of catheter lab workspaces. In addition, wireless intraluminal imaging devices may be stored in a sterile area when not in use, and thus may conform to the sterilization requirements of a catheter lab.

FIG. 1 is a schematic diagram of a wireless intraluminal imaging system 100, according to aspects of the present disclosure. The system 100 may include a wireless intraluminal imaging device 102, a wireless communication component 122, an image processing system 124, such as a console and/or a computer, and a monitor 126. The intraluminal imaging device 102 may include a flexible elongate member 106, which may be a catheter, a guide wire, or a guide catheter, coupled to a wireless communication component 104.

The intraluminal imaging device 102 may further include an ultrasound imaging assembly 110 and an electrical cable 112. The ultrasound imaging assembly 110 may be mounted at a distal portion 131 near a distal end of the flexible elongate member 106. The wireless communication component 104 may be mounted near a proximal end of the flexible elongate member 106. The wireless communication component 104 is in wireless communication with the wireless communication component 122 over a radio frequency (RF) link, as shown by the RF signals 150. The electrical cable 112 extends between the ultrasound imaging assembly 110 and the wireless communication component 104. The electrical cable 112 may carry control signals, echo data, and/or power between various components of the intraluminal imaging device 102 as described in greater detail herein.

At a high level, the intraluminal imaging device 102 emits ultrasonic energy from a transducer array included in the ultrasound imaging assembly 110. The ultrasonic energy is reflected by tissue structures in the medium, such as a vessel 120, surrounding the ultrasound imaging assembly 110, and the ultrasound echo signals are received by the transducer array in the ultrasound imaging assembly 110. The electrical cable 112 transfers the ultrasound echo signals to the wireless communication component 104. The wireless communication component 104 wirelessly transmits the ultrasound echo signals, for example, in a RF band. Upon receiving the ultrasound echo signals, the wireless communication component 122 transfers the ultrasound echo signals to the image processing system 124, where the ultrasound image is reconstructed and displayed on the monitor 126. The ultrasound imaging assembly 110, the wireless communication component 104, and associated components for signal controls and transfers are described in greater detail herein.

The image processing system 124 can include a processor and a memory. The image processing system 124 can be operable to facilitate the features of the system 100 described herein. For example, the processor can execute computer readable instructions stored on the non-transitory tangible computer readable medium.

In an embodiment, the image processing system 124 outputs image data of an image of a vessel, such as a cross-sectional image of the vessel 120, and the monitor 126 displays the image. The vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the intraluminal imaging device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the intraluminal imaging device 102 may be used to examine man-made structures such as, but without limitation, heart valves, stents, shunts, filters and other devices.

In an embodiment, the intraluminal imaging device 102 further includes a guide wire exit port 116 disposed near a junction 130 at which a distal portion 131 is coupled to a proximal portion 132. Accordingly, in some instances the intraluminal imaging device 102 is a rapid-exchange catheter. The guide wire exit port 116 allows a guide wire 118 to be inserted towards the distal end in order to direct the intraluminal imaging device 102 through the vessel 120.

In an embodiment, the system 100 may generate images at a frame rate of about 20 frames to about 40 frames per second. For example, each frame includes an 8-bit grayscale image in the order of about 512 by 512 pixels to about 832 by 832 pixels. In another embodiment, the system 100 may be a high-definition (HD)-IVUS system and may generate images at a frame rate of about 60 frames per second. Each frame may include about more than 1000 by 1000 pixels. Thus, the wireless communication components 104 and 122 may operate at a high data rate of about 1 gigabits per second (Gbps) to about 10 Gbps. Some examples of high-data rate wireless communication protocols may include Institute of Electrical and Electronics Engineers (IEEE) 802.11ad and ultra-wideband (UWB). Alternatively, the intraluminal imaging device 102 may include additional compression component for compressing the echo data prior to transmitting the echo data over the RF link, and thus a lower-data rate wireless communication protocol may be used instead.

The system 100 supports bidirectional communications. For example, the wireless communication component 122 encodes the control signals generated by the image processing system 124 for wireless transmission to the intraluminal imaging device 102. At the intraluminal imaging device 102, the wireless communication component 104 receives the encoded control signals and recovers the control signals, which may be used to control the ultrasound imaging assembly 110. In a reverse direction, the wireless communication component 104 encodes ultrasound echo signals collected by the ultrasound imaging assembly 110 for wireless transmission to the wireless communication component 122. Upon receiving the encoded ultrasound echo signals, the wireless communication component 122 recovers the ultrasound echo signals, which may be used for image generation at the image processing system 124 and display at the monitor 126. In some embodiments, the wireless communication components 104 and 122 may include substantially similar functional components, but may have different physical form factors and arrangements.

The system 100 may use any of a variety of ultrasonic imaging technologies. Accordingly, in some embodiments of the present disclosure, the system 100 is a solid-state IVUS imaging system incorporating an array of piezoelectric transducers fabricated from lead-zirconate-titanate (PZT) ceramic. In some embodiments, the system 100 incorporates capacitive micromachined ultrasonic transducers (CMUTs), or piezoelectric micromachined ultrasound transducers (PMUTs).

Figure 3:
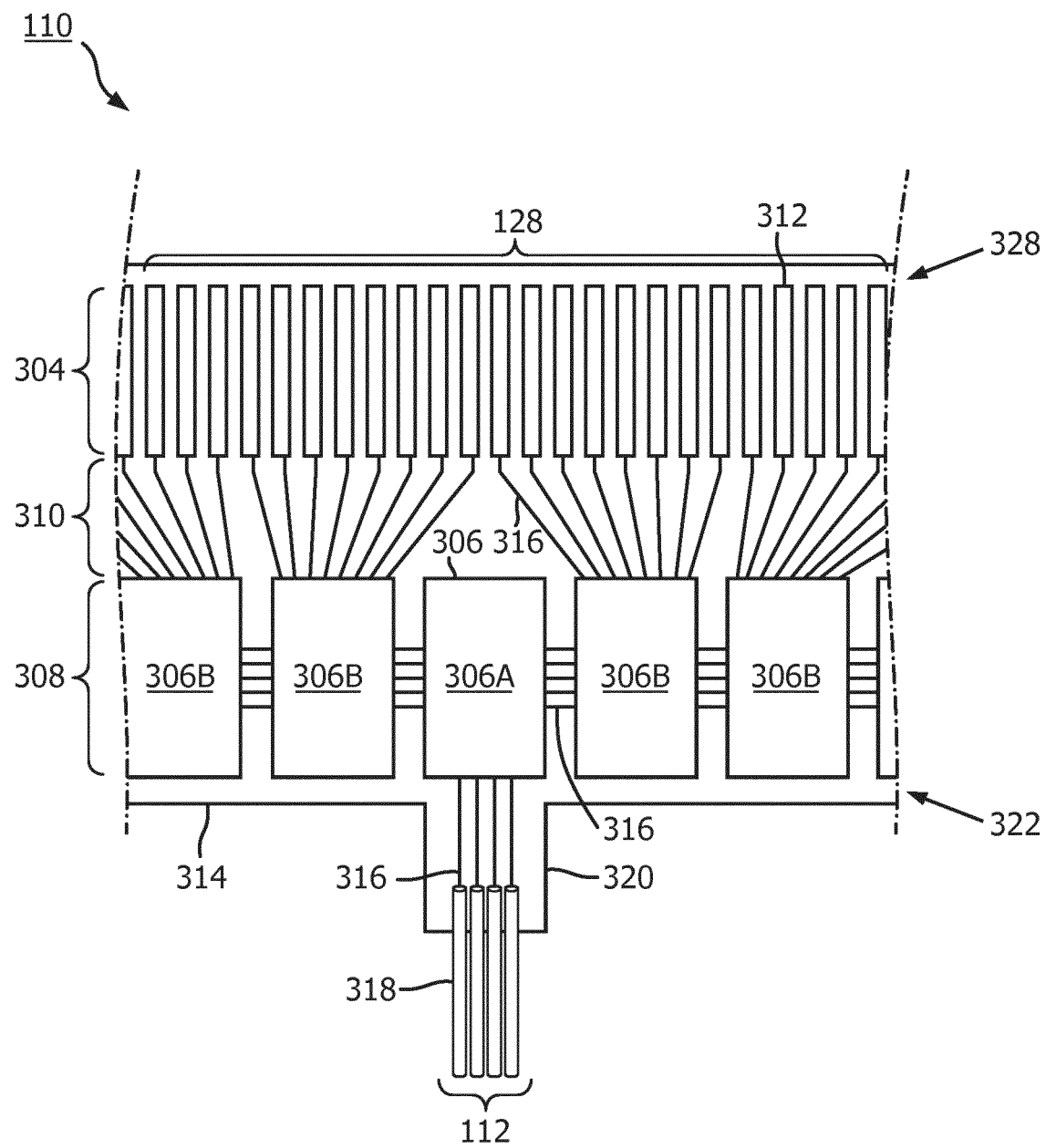
FIG. 3 is a top view of a portion of an intraluminal imaging assembly in a flat configuration, according to aspects of the present disclosure.

In some embodiments, the system 100 includes some features similar to traditional solid-state IVUS system, such as the EagleEye® catheter available from Volcano Corporation and those disclosed in U.S. Pat. No. 7,846,101 hereby incorporated by reference in its entirety. For example, the intraluminal imaging device 102 includes the ultrasound imaging assembly 110 near a distal end of the intraluminal imaging device 102 and an electrical cable 112 extending along the longitudinal body of the intraluminal imaging device 102. The cable 112 is a transmission line bundle including a plurality of conductors, including one, two, three, four, five, six, seven, or more conductors 318 (FIG. 3). It is understood that any suitable gauge wire can be used for the conductors 318. In an embodiment, the cable 112 can include a four-conductor transmission line arrangement with, e.g., 41 American wire gauge (AWG) wires. In an embodiment, the cable 112 can include a seven-conductor transmission line arrangement utilizing, e.g., 44 AWG wires. In some embodiments, 43 AWG wires can be used.

Figure 2:
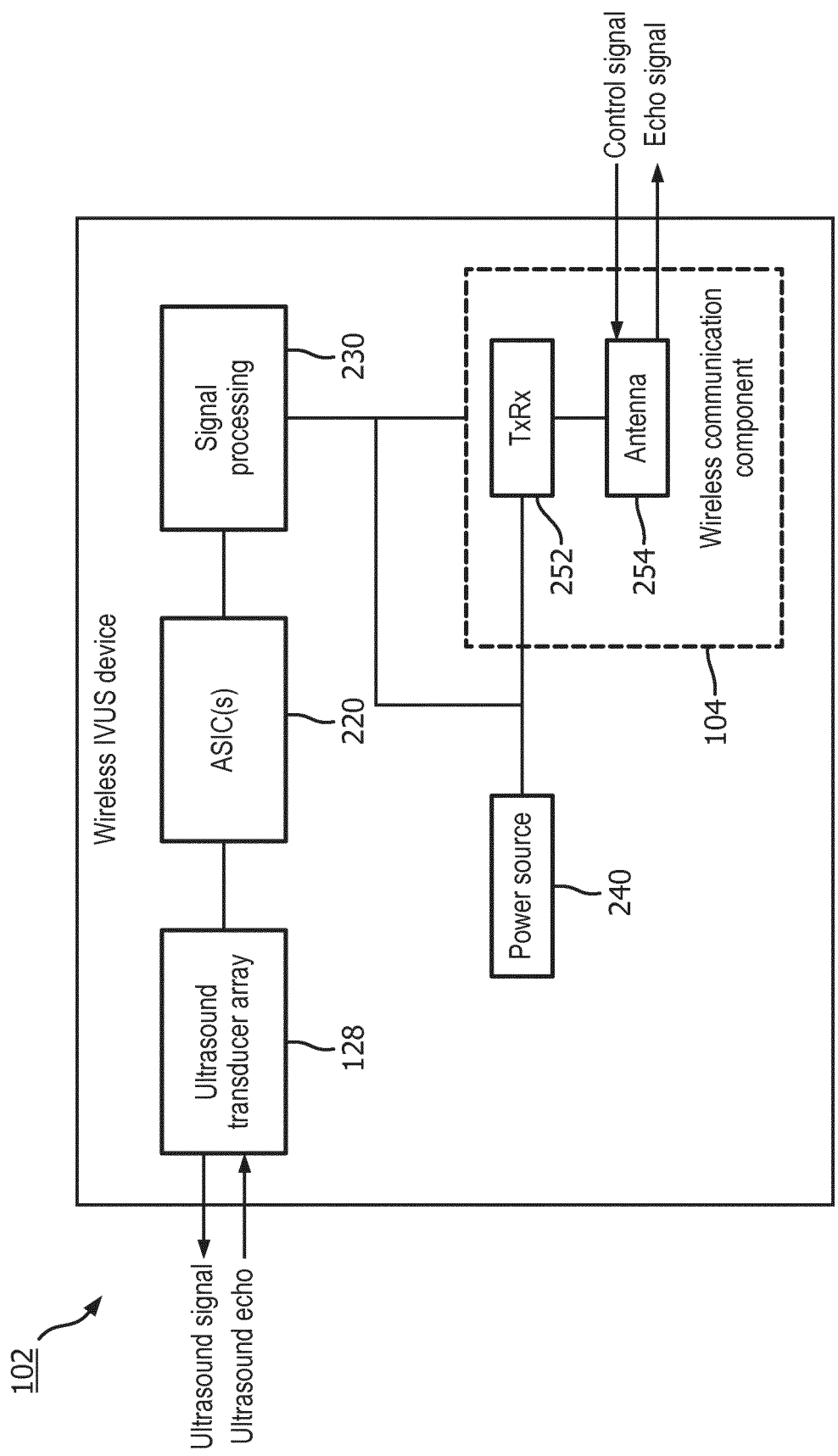
FIG. 2 is a schematic diagram illustrating a wireless intraluminal imaging device architecture, according to aspects of the present disclosure.

FIG. 2 is a schematic diagram illustrating the wireless intraluminal imaging device 102 architecture, according to aspects of the present disclosure. FIG. 2 provides a more detail view of the internal components of the intraluminal imaging device 102. As shown, the intraluminal imaging device 102 includes an ultrasound transducer array 128, one or more application specific integrated circuits (ASICs) 220, a signal processing component 230, a power source 240, and the wireless communication component 104. The power source 240 may be a battery pack or any suitable electrical energy storage that powers the transducer array 128, the ASIC 220, the signal processing component 230, and the wireless communication component 104. The ASIC 220 is in communication with the ultrasound transducer array 128 and the signal processing component 230, for example, over the electrical cable 112. The signal processing component 230 is in further communication with the wireless communication component 104, for example, over the electrical cable 112 or another cable. The communication may be bidirectional including both control signals for operating the intraluminal imaging device 102 and echo data collected from the ultrasound transducer array 128. The ultrasound transducer array 128 and the ASIC 220 may be included in the ultrasound imaging assembly 110. The signal processing component 230, the power source 240, and the wireless communication component 104 may be arranged in various configurations near the proximal end of the intraluminal imaging device 102 as described in greater detail herein.

The ultrasound transducer array 128 emits ultrasound signals and receives echoes from the emitted ultrasound signals, for example, reflected by surrounding tissues such as the vessel 120, based on commands and/or triggers received from the ASIC 220. The ASIC 220 controls and coordinates the operations of the ultrasound transducer array 128. For example, the ASIC 220 may switch an individual transducer or a subset of the transducers in the ultrasound transducer array 128 from a transmit mode to a receive mode or from an active mode to an inactive mode. The ASIC 220 may control the transmission and/or reception of the transducers for beamforming. The ASIC 220 may multiplex and transfer the echo signals to the signal processing component 230.

The signal processing component 230 may include hardware and/or software configured to condition the echo signals prior to transmission to the image processing system 124. Signal conditioning may include analog and/or digital processing. Signal conditioning may include filtering, amplification, aggregation, and/or compression. In some embodiments, the signal processing component 230 may include analog-to-digital converters (ADCs), digital-to-analog converters (DACs), and a digital signal processor. For example, the ADCs may convert analog electrical signals received from the ultrasound transducer array 128 into digital signals. The digital signal processor may perform digital signal conditioning on the digital signals. The DACs may convert the digital conditioned signals into analog signals for transmission to the wireless communication component 104. The ADCs, DACs, and digital signal processor may perform similar operations in a reverse direction along a receiving path from the wireless communication component 104. In some embodiments, the intraluminal imaging device 102 may include buffers between the wireless communication component 104 and the signal processing component 230 for buffering input signals received from the wireless communication component 104 or output signals for transmission via the wireless communication component 104.

In an embodiment, the signal processing component 230 facilitates communication of signals received from the image processing system 124 (e.g., via the wireless communication component 104) and the ASIC 220. In some embodiments, the signal processing component 230 may include operations that are typically performed at a patient interface module (PIM) of a wired intraluminal imaging device. In such embodiments, the communication includes the steps of: (1) providing commands to the ASIC 220 to select the particular transducer array element(s) to be used for transmit and receive, (2) providing the transmit trigger signals to the ASIC 220 to activate the transmitter circuitry to generate an electrical pulse to excite the selected transducer array element(s), and/or (3) accepting amplified echo signals received from the selected transducer array element(s) via amplifiers included on the ASIC 220. In some embodiments, the functionalities and/or operations of the ASIC 220 and the signal processing component 230 may be integrated or alternatively distributed to achieve similar functionalities.

The wireless communication component 104 includes a transceiver (Tx/Rx) 252 and an antenna 254. The transceiver 252 may include hardware and/or software configured to perform data framing, data encoding/decoding, scrambling/descrambling, modulation/demodulation, and/or error encoding/decoding, for example, according to a pre-determined wireless communication protocol, such as IEEE 802.11ad or UWB. The antenna 254 may be constructed from a metal thin film or a metal thin wire. In some embodiments, the antenna 254 may be an antenna array, which may allow for beamforming and directional transmission. In some embodiments, the antenna array may transmit and receive signals in the 60 gigahertz (GHz) band. The antenna 254 may have any suitable dimension. In some embodiments, the antenna 254 may have a length between about 0.5 millimeter (mm) and about 10 mm, with some particular embodiments between about 1 mm and 3 mm.

Although not shown, the intraluminal imaging device 102 may include other components and/or circuitries, such as voltage signal converters, ADCs, DACs, line drivers, encoder/decoder logics, and over voltage and/or electrostatic discharge (ESD) protection devices (e.g., diodes), for facilitating the operations of the intraluminal imaging device 102.

Figure 4:
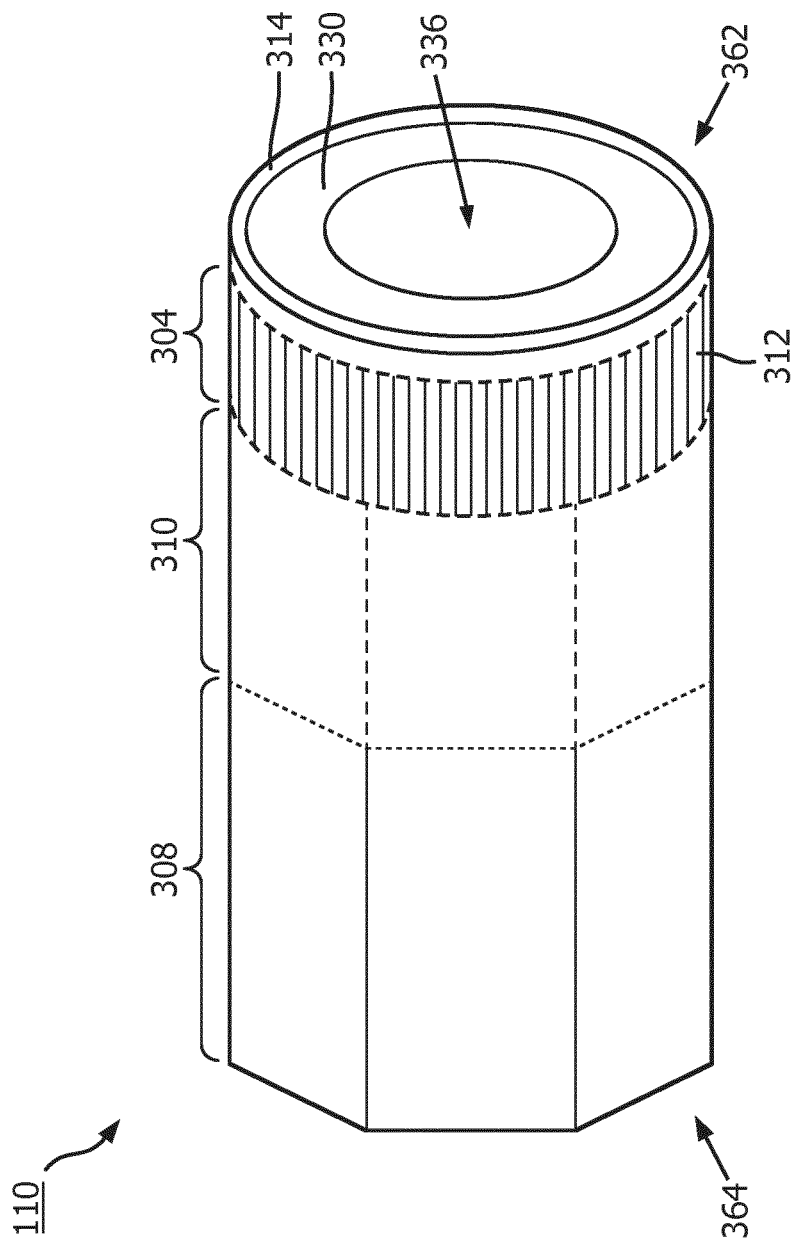
FIG. 4 is a perspective view of an intraluminal imaging assembly, including a flex circuit in a rolled configuration around a support member, according to aspects of the present disclosure.

FIG. 3 is a top view of a portion of the ultrasound imaging assembly 110 in a flat configuration, according to aspects of the present disclosure. The ultrasound imaging assembly 110 includes the transducer array 128 formed in a transducer region 304 and transducer control logic dies 306 (including dies 306A and 306B) formed in a control region 308, with a transition region 310 disposed therein between. The transducer array 128 includes an array of transducers 312. The transducer control logic dies 306 may correspond to the ASIC(s) 220. The transducer control logic dies 306 and the transducers 312 are mounted on a flex circuit 314 in a flat form prior to assembling into a final rolled form (FIG. 4). The transducer array 128 is a non-limiting example of a medical sensor element and/or a medical sensor element array. The transducer control logic dies 306 is a non-limiting example of a control circuit. While the ultrasound imaging assembly 110 is described as including a flex circuit, it is understood that the transducers and/or controllers may be arranged to form the ultrasound imaging assembly 110 in other configurations, including those omitting a flex circuit.

The transducer array 128 can include any number and type of ultrasound transducers 312, although for clarity only a limited number of ultrasound transducers are illustrated in FIG. 3. In an embodiment, the transducer array 128 includes 32 individual ultrasound transducers 312. In another embodiment, the transducer array 128 includes 64 ultrasound transducers 312. In another embodiment, the transducer array 128 includes 96 ultrasound transducers 312. In yet another embodiment, the transducer array 128 includes 128 ultrasound transducers 312. Other numbers are both contemplated and provided for. With respect to the types of transducers, in an embodiment, the ultrasound transducers 312 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array 128 includes PZT transducers such as bulk PZT transducers, capacitive micromachined ultrasound transducers (cMUTs), single crystal piezoelectric materials, other suitable ultrasound transmitters and receivers, and/or combinations thereof.

The ultrasound imaging assembly 110 may include various transducer control logic, which in the illustrated embodiment is divided into discrete control logic dies 306. In various examples, the control logic of the ultrasound imaging assembly 110 performs: decoding control signals sent by the signal processing component 230 across the cable 112, driving one or more transducers 312 to emit an ultrasonic signal, selecting one or more transducers 312 to receive a reflected echo of the ultrasonic signal, amplifying a signal representing the received echo, and/or transmitting the signal to the signal processing component 230 across the cable 112. In some embodiments, when the transducer array 128 includes cMUTs, the control logic may further include biasing circuitries to optimize the cMUTs for transmit and/or receive. In the illustrated embodiment, an ultrasound imaging assembly 110 having 64 ultrasound transducers 312 divides the control logic across nine control logic dies 306, of which five are shown in FIG. 3. Designs incorporating other numbers of control logic dies 306 including 8, 9, 16, 17 and more are utilized in other embodiments. In general, the control logic dies 306 are characterized by the number of transducers they are capable of driving, and exemplary control logic dies 306 drive 4, 8, and/or 16 transducers.

The control logic dies 306 are not necessarily homogenous. In some embodiments, a single controller is designated a master control logic die 306A and contains the communication interface for the cable 112. Accordingly, the master control circuit may include control logic that decodes control signals received over the cable 112, transmits control responses over the cable 112, amplifies echo signals, and/or transmits the echo signals over the cable 112. The remaining controllers are slave controllers 306B. The slave controllers 306B may include control logic that drives a transducer 312 to emit an ultrasonic signal and selects a transducer 312 to receive an echo. In the depicted embodiment, the master controller 306A does not directly control any transducers 312. In other embodiments, the master controller 306A drives the same number of transducers 312 as the slave controllers 306B or drives a reduced set of transducers 312 as compared to the slave controllers 306B. In an exemplary embodiment, a single master controller 306A and eight slave controllers 306B are provided with eight transducers assigned to each slave controller 306B.

The flex circuit 314, on which the transducer control logic dies 306 and the transducers 312 are mounted, provides structural support and interconnects for electrical coupling. The flex circuit 314 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In the flat configuration illustrated in FIG. 3, the flex circuit 314 has a generally rectangular shape. As shown and described herein, the flex circuit 314 is configured to be wrapped around a support member 330 (FIG. 4) to form a cylindrical toroid in some instances. Therefore, the thickness of the film layer of the flex circuit 314 is generally related to the degree of curvature in the final assembled ultrasound imaging assembly 110. In some embodiments, the film layer is between 5 micrometers (μm) and 100 μm, with some particular embodiments being between 12.7 μm or 0.5 milliinch (mil) and 25.1 μm or 1.0 mil.

To electrically interconnect the control logic dies 306 and the transducers 312, in an embodiment, the flex circuit 314 further includes conductive traces 316 formed on the film layer that carry signals between the control logic dies 306 and the transducers 312. In particular, the conductive traces 316 providing communication between the control logic dies 306 and the transducers 312 extend along the flex circuit 314 within a transition region 310 between the transducer region 304 and the control region 308. In some instances, the conductive traces 316 can also facilitate electrical communication between the master controller 306A and the slave controllers 306B. The conductive traces 316 can also provide a set of conductive pads that contact the conductors 318 of cable 112 when the conductors 318 of the cable 112 are mechanically and electrically coupled to the flex circuit 314.

Suitable materials for the conductive traces 316 include copper, gold, aluminum, silver, tantalum, nickel, and tin, and may be deposited on the flex circuit 314 by processes such as sputtering, evaporation, plating, wet chemical etching, reactive ion etching (RIE) (e.g., a chemical etching), ion beam etching (e.g., physical etching), physical vapor deposition, chemical vapor deposition, and/or liquid phase deposition). In an embodiment, the flex circuit 314 includes a chromium adhesion layer. The width and thickness of the conductive traces 316 are selected to provide proper conductivity and resilience when the flex circuit 314 is rolled. In that regard, an exemplary range for the thickness of a conductive trace 316 and/or conductive pad is between 10-50 µm. For example, in an embodiment, 20 µm conductive traces 316 are separated by 20 µm of space. The width of a conductive trace 316 on the flex circuit 314 may be further determined by the width of the conductor 318 to be coupled to the trace/pad.

The flex circuit 314 can include a conductor interface 320 in some embodiments. The conductor interface 320 can be a location of the flex circuit 314 where the conductors 318 of the cable 112 are coupled to the flex circuit 314. For example, the bare conductors of the cable 112 are electrically coupled to the flex circuit 314 at the conductor interface 320. The conductor interface 320 can be tab extending from the main body of flex circuit 314. In the illustrated embodiment, the conductor interface 320 extends from the proximal portion 322 of the flex circuit 314. In other embodiments, the conductor interface 320 is positioned at other parts of the flex circuit 314, such as the distal portion 328, or the flex circuit 314 omits the conductor interface 320. In some embodiments, the substrate forming the conductor interface 320 is made of the same material(s) and/or is similarly flexible as the flex circuit 314. In other embodiments, the conductor interface 320 is made of different materials and/or is comparatively more rigid than the flex circuit 314. For example, the conductor interface 320 can be made of a plastic, thermoplastic, polymer, hard polymer, etc., including polyoxymethylene (e.g., DELRIN®), polyether ether ketone (PEEK), nylon, and/or other suitable materials.

In some instances, the scanner assembly 110 is transitioned from a flat configuration (FIG. 3) to a rolled or more cylindrical configuration (FIG. 4). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety. FIG. 4 is a perspective view with the flex circuit 314 in the rolled configuration around the support member 330, according to aspects of the present disclosure. The support member 330 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, ('220 application) the entirety of which is hereby incorporated by reference herein. The support member 330 can be a ferrule having a distal portion 362 and a proximal portion 364. The support member 330 can be a ferrule having a distal portion 362 and a proximal portion 364. The support member 330 can be tubular in shape and define a lumen 336 extending longitudinally therethrough. The lumen 336 can be sized and shaped to receive the guide wire 118. The support member 330 can be manufactured using any suitable process. For example, the support member 330 can be machined, such as by removing material from a blank to shape the support member 330, or molded, such as by an injection molding process or three-dimensional (3D) printing.

Figure 5:
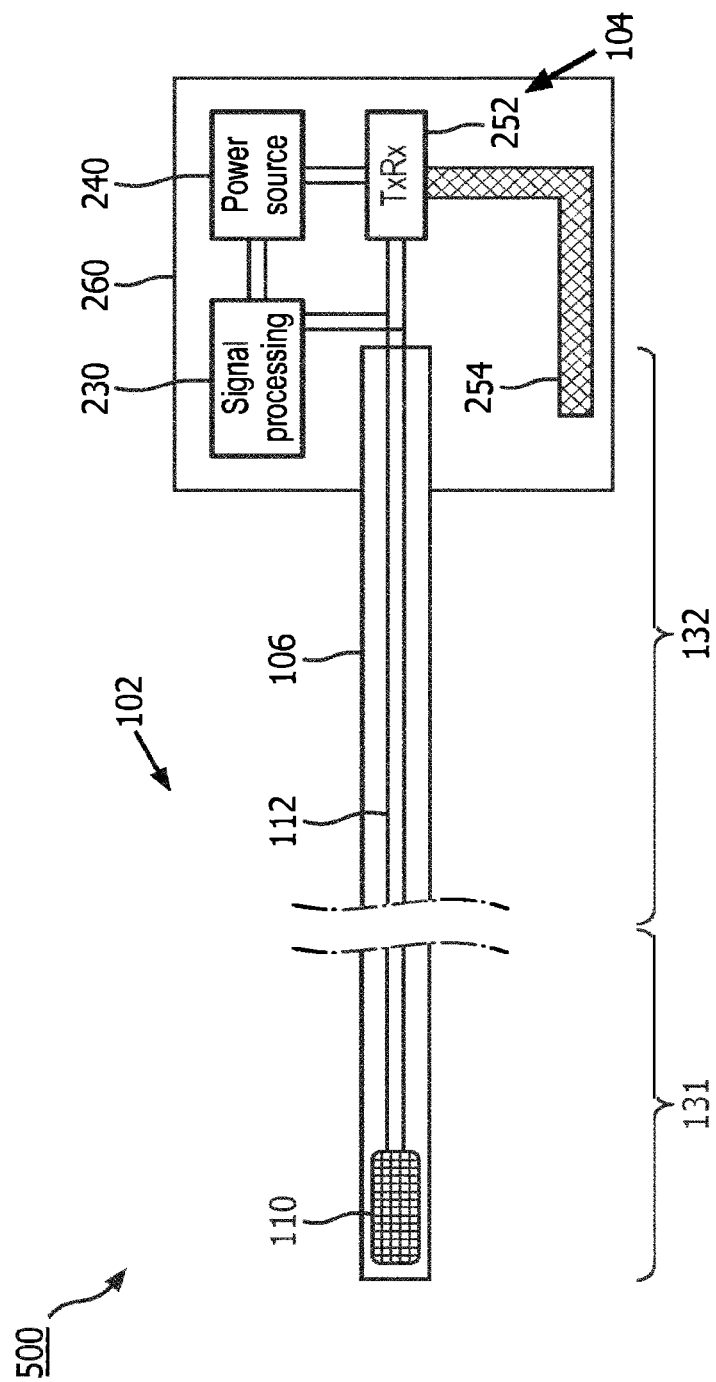
FIG. 5 is a schematic diagram illustrating a configuration of a wireless intraluminal imaging device, according to aspects of the present disclosure.
Figure 6:
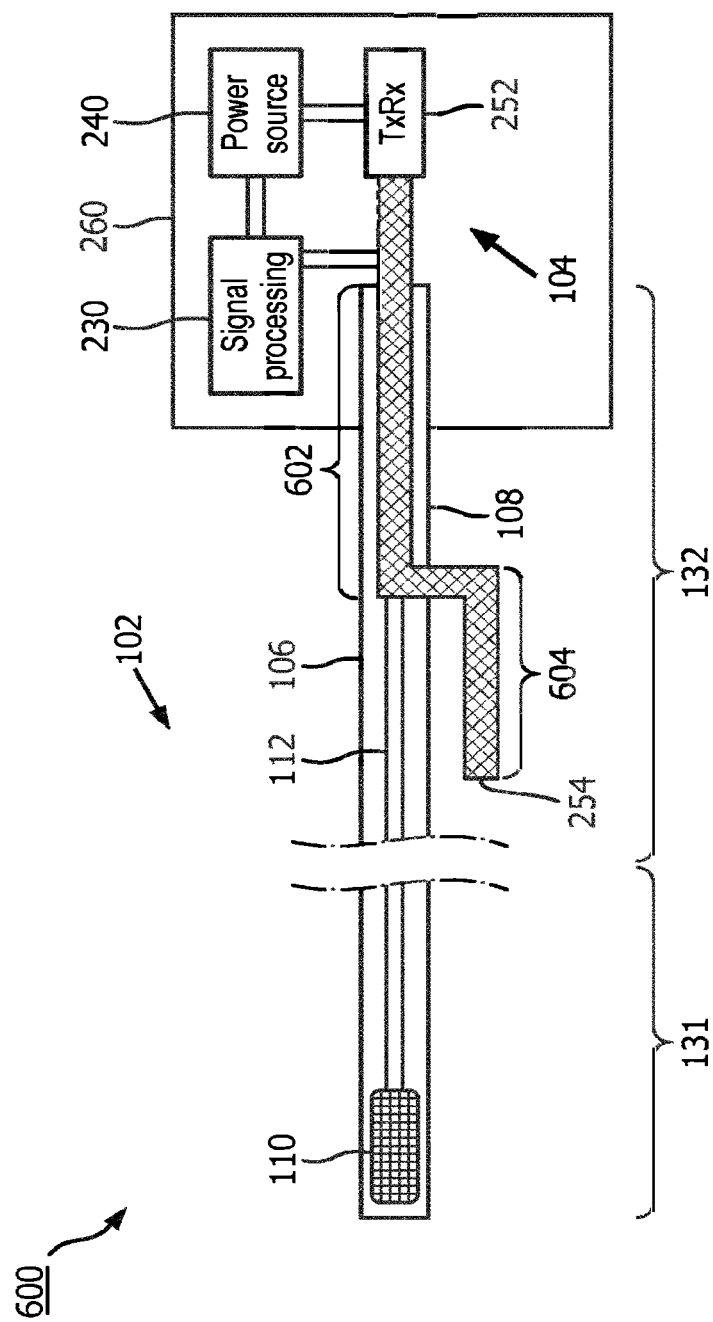
FIG. 6 is a schematic diagram illustrating a configuration of a wireless intraluminal imaging device, according to aspects of the present disclosure.
Figure 7:
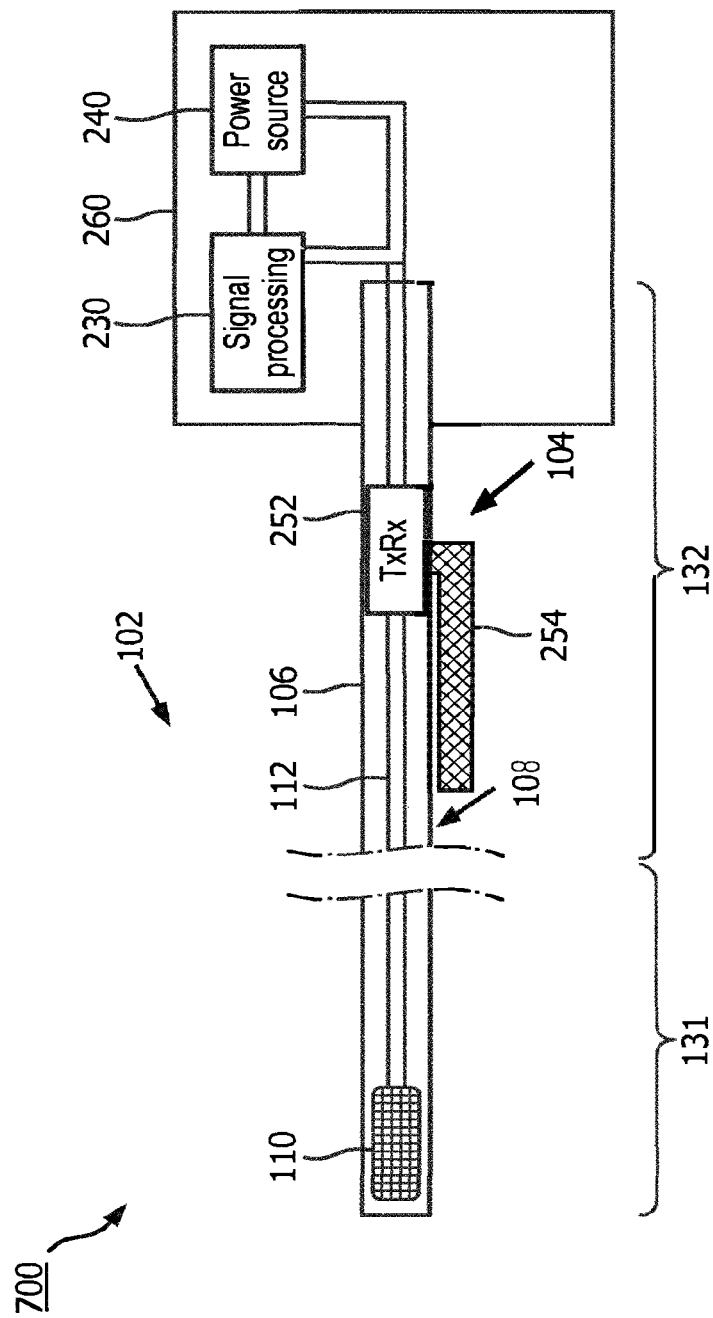
FIG. 7 is a schematic diagram illustrating a configuration of a wireless intraluminal imaging device, according to aspects of the present disclosure.

FIGS. 5-7 illustrate several configurations for placing or positioning the components, such as the signal processing component 230, the power source 240, and the wireless communication component 104, within the intraluminal imaging device 102. In operation, the intraluminal imaging device 102 is brought into position in a patient body by sliding the flexible elongate member 106 along the guide wire 118 that is put into position earlier. The proximal portion 132 may remain outside the patient body. In an embodiment, the intraluminal imaging device 102 may include a handle coupled to the proximal end of the flexible elongate member 106. The handle may be sized for hand control. For example, a physician may hold the handle while advancing the flexible elongate member 106 into a vessel of the patient body and/or rotating the ultrasound imaging assembly 110. The handle may accommodate various components, such as the power source 240, for operating the intraluminal imaging device 102. The power source 240 may be a lithium battery or any suitable electrical energy source. In an embodiment, the power source 240 may have an electrical storage capacity between about 1 ampere hours (Ahr) and about 5 Ahr, and in some particular embodiments, the power source 240 may have a minimum of 2 Ahr of electrical storage capacity. Dimensions of the power source 240 may vary depending on the capacity and structure of the handle in which the power source 240 will be used. In some embodiments, the power source 240 may be charged using a wireless inductive charger, such as a Qi wireless inductive charger.

FIG. 5 is a schematic diagram illustrating a configuration 500 of the intraluminal imaging device 102, according to aspects of the present disclosure. In the configuration 500, the ultrasound imaging assembly 110 including the ultrasound transducer array 128 and the ASIC(s) 220 is positioned at the distal portion 131 of the flexible elongate member 106 near the distal end. For example, the ultrasound transducer array 128 and the ASIC(s) 220 are configured in a similar rolled configuration as shown in FIG. 4. The signal processing component 230, the power source 240, the transceiver 252, and the antenna 254 are positioned within a handle 260 coupled to the proximal portion 132 of the flexible elongate member 106 at the proximal end. As shown, the antenna 254 extends from the transceiver 252 and terminates within the handle 260. In an embodiment, the ultrasound imaging assembly 110, the signal processing component 230, the power source 240, and the transceiver 252 are connected via the electrical cable 112 and/or additional cables.

FIG. 6 is a schematic diagram illustrating a configuration 600 of the intraluminal imaging device 102, according to aspects of the present disclosure. Similar to the configuration 500, the ultrasound imaging assembly 110 including the ultrasound transducer array 128 and the ASIC(s) 220 is positioned near the distal end of the flexible elongate member 106, and the signal processing component 230, the power source 240, and the transceiver 252 are positioned within the handle 260 coupled to the proximal end of the flexible elongate member 106. However, the antenna 254 is positioned near the handle 260 and extends distally along the proximal portion 132 of the flexible elongate member 106 instead of terminating within the handle 260. In other embodiments, the antenna 254 may extend in any suitable direction. Thus, the configuration 600 can accommodate any antenna length limited by the length of the proximal portion 132 so that the antenna 254 may be positioned outside of a patient body when in use. For example, the antenna 254 may extend within the flexible elongate member 106 for a length 602 and along an outer surface 108 of the flexible elongate member 106 for a length 604. The lengths 602 and 604 may vary depending on the length of the antenna 254. In some embodiments, the antenna 254 may extend along the outer surface 108 such that a surface or a portion of the antenna 254 is exposed to ambient. In some other embodiments, the antenna 254 may be positioned close to the exterior surface of the flexible elongate member 106, but sealed by a coating or polymer layer such that the antenna 254 is not exposed to the ambient. One advantage of positioning a portion of the antenna 254 along the outer surface 108 is that the antenna 254 may have line of sight when operating at high frequencies (e.g., greater than 60 GHz) instead of blocked by a physician's hand holding the handle 260.

FIG. 7 is a schematic diagram illustrating a configuration 700 of the intraluminal imaging device 102, according to aspects of the present disclosure. Similar to the configuration 600, the ultrasound imaging assembly 110 including the ultrasound transducer array 128 and the ASIC(s) 220 is positioned near the distal end of the flexible elongate member 106, and the signal processing component 230 and the power source 240 are positioned within the handle 260 coupled to the proximal end of the flexible elongate member 106. However, the transceiver 252 and the antenna 254 are positioned within flexible elongate member 106 at the proximal portion 132 adjacent to the handle 260. The antenna 254 extends from the transceiver 252 along an outer surface 108 of the flexible elongate member 106. The antenna 254 may extend towards the distal end of the device 102, the proximal end of the device 102, or in any suitable direction. Compare to the configuration 600, the transceiver 252 is moved from the handle 260 to be closer to the antenna 254 in the configuration 700, and thus transmission efficiency may be improved.

FIG. 8 is a signaling diagram of a method 800 of signal transfer in the intraluminal imaging device 102, according to aspects of the present disclosure. The method 800 is implemented when the intraluminal imaging device 102 is in use for imaging tissue of a patient body. Steps of the method 800 can be executed by the wireless communication component 104, the signal processing component 230, and the ultrasound transducer array 128 of the intraluminal imaging device 102. In some embodiments, the signal processing component 230 may be integrated with functionalities of the ASICs 220. The method 800 can be better understood with reference to FIGS. 2 and 5-7. As illustrated, the method 800 includes a number of enumerated steps, but embodiments of the method 800 may include additional steps before, after, and in between the enumerated steps. In some embodiments, one or more of the enumerated steps may be omitted or performed in a different order.

At step 805, the wireless communication component 104 receives a first wireless signal carrying an instruction, for example, from the external wireless communication component 122 via an RF link. The instruction may be originated from the image processing system 124. The signal may be encoded and modulated according to a pre-determined wireless communication protocol. The wireless communication component 104 may perform demodulation and decoding on the received signal to recover the instruction. At step 810, the wireless communication component 104 forwards the instruction to the signal processing component 230.

At step 815, the signal processing component 230 processes the instruction. The signal processing component 230 may generate a first control signal based on the instruction. At step 820, the signal processing component 230 transmits the first control signal (e.g., internally over the cable 112 via the ASICs 220), to the ultrasound transducer array 128. For example, the first control signal may activate one or more ultrasound transducers 312 of the transducer array 128, switch the ultrasound transducers 312 to a transmit mode, and trigger the ultrasound transducers 312 to emit ultrasound beams.

At step 825, the transducer array 128 (e.g., one or more transducers 312) transmits ultrasound beams, which may include a sequence of pulses. When the ultrasound beams reach tissues and structures near and/or surrounding the transducer array 128, portions of the transmitted ultrasound beams are reflected by the tissues, generating ultrasound echoes.

At step 830, the signal processing component 230 transmits a second control signal (e.g., internally over the cable 112 via the ASICs 220) to the ultrasound transducer array 128 to switch one or more transducers 312 to a receive mode. At step 835, the ultrasound transducer array 128 receives the ultrasound echoes. At step 840, the ultrasound transducer array 128 transmits an ultrasound echo signal obtained from the ultrasound echoes to the signal processing component 230, for example, via the ASICs 220.

At step 845, the signal processing component 230 conditions the ultrasound echo signal. For example, the signal processing component 230 may perform filtering, amplification, compression, and/or any pre-processing on the ultrasound echo signal. In some embodiments, the amplification may be time-gain-controlled (TGC). At step 850, the signal processing component 230 transmits the conditioned signal to the wireless communication component 104.

At step 855, the wireless communication component 104 transmits a second wireless signal carrying the conditioned signal, for example, externally to the wireless communication component 122. The wireless communication component 104 may generate the second wireless signal by encoding the conditioned signal according to the pre-determined wireless communication protocol. Subsequently, the wireless communication component 122 may transfer the conditioned signal to the image processing system 124 for generating images, which may be displayed on the monitor 126.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A wireless intraluminal imaging device, comprising:
an intraluminal catheter comprising a flexible elongate member configured to be positioned within a blood vessel, a proximal portion, a distal portion, and an outer surface of an individual component of the intraluminal catheter, wherein the individual component is the flexible elongate member such that the outer surface extends between the proximal portion and the distal portion, wherein the proximal portion is configured to remain outside of a patient when the intraluminal catheter is positioned within the blood vessel;

an ultrasound imaging assembly positioned at the distal portion of the intraluminal catheter and configured to obtain intravascular ultrasound imaging data;

a cable coupled to the ultrasound imaging assembly and extending along the intraluminal catheter; and a wireless communication hardware coupled to the proximal portion of the intraluminal catheter, the wireless communication hardware in communication with the ultrasound imaging assembly via the cable, wherein the wireless communication hardware comprises a transceiver and an antenna, wherein the antenna is coupled to the transceiver, wherein the antenna extends from the transceiver along the proximal portion of the intraluminal catheter such that the antenna is disposed on a portion of the outer surface of the intraluminal catheter that remains outside of the patient, wherein the antenna is configured to receive and/or transmit wireless data signals associated with the ultrasound imaging assembly while the antenna is positioned outside of the patient.

2. The wireless intraluminal imaging device of claim 1, wherein the transceiver is coupled to the cable.

3. The wireless intraluminal imaging device of claim 2, further comprising a handle coupled to a proximal end of the proximal portion of the intraluminal catheter, wherein the handle includes a power source coupled to the cable, and wherein the power source powers the ultrasound imaging assembly and the wireless communication hardware via the cable.

4. The wireless intraluminal imaging device of claim 3, wherein the transceiver and the antenna are positioned at least partially within the handle.

5. The wireless intraluminal imaging device of claim 3, wherein the transceiver is positioned within the handle, and wherein the antenna extends distally from the transceiver and along the proximal portion of the intraluminal catheter.

6. The wireless intraluminal imaging device of claim 3, wherein the transceiver is positioned within the intraluminal catheter such that the transceiver and an end of the antenna coupled to the transceiver are spaced from the handle.

7. The wireless intraluminal imaging device of claim 3, further comprising a signal processor positioned within the handle and in communication with the ultrasound imaging assembly and the transceiver.

8. The wireless intraluminal imaging device of claim 7, wherein the power source provides power to the signal processor.

9. The wireless intraluminal imaging device of claim 7, wherein the signal processor controls transmission and reception by the ultrasound imaging assembly and conditions ultrasound echo signals collected by the ultrasound imaging assembly.

10. The wireless intraluminal imaging device of claim 9, wherein the signal processor conditions the ultrasound echo signals by performing at least one of a filtering, amplifying, aggregating, or compressing of the ultrasound echo signals.

11. The wireless intraluminal imaging device of claim 9, wherein the transceiver receives the conditioned ultrasound echo signals from the signal processor and wirelessly transmits the conditioned ultrasound echo signals via the antenna such that the wireless data signals comprise the conditioned ultrasound echo signals.

12. The wireless intraluminal imaging device of claim 9, wherein the wireless data signals comprise an instruction, wherein the transceiver wirelessly receives the instruction via the antenna and transmits the instruction to the signal processor, and wherein the signal processor controls at least one of the transmission or the reception of the ultrasound imaging assembly based on at least the instruction.

13. The wireless intraluminal imaging device of claim 1, wherein the wireless communication hardware transmits and receives the wireless data signals at a data rate of at least 1 gigabits per second.

14. The wireless intraluminal imaging device of claim 1, wherein the wireless communication hardware wirelessly transmits and receives the wireless data signals at a frequency greater than about 60 gigahertz.

15. A wireless intraluminal imaging system, comprising:
an intraluminal imaging device including:
an intraluminal catheter comprising a flexible elongate member configured to be positioned within a blood vessel, a proximal portion, a distal portion, an outer surface of an individual component of the intraluminal catheter, wherein the individual component is the flexible elongate member such that the outer surface extends between the proximal portion and the distal portion, wherein the proximal portion is configured to remain outside of a patient when the intraluminal catheter is positioned within the blood vessel;

an ultrasound imaging assembly positioned at the distal portion of the intraluminal catheter and configured to obtain intravascular ultrasound imaging data;

a cable coupled to the ultrasound imaging assembly and extending along the intraluminal catheter; and a first wireless communication hardware coupled to the proximal portion of the intraluminal catheter, wherein the first wireless communication hardware is in communication with the ultrasound imaging assembly via the cable, wherein the first wireless communication hardware comprises a transceiver and an antenna, wherein the antenna is coupled to the transceiver, wherein the antenna extends from the transceiver along the proximal portion of the intraluminal catheter such that the antenna is disposed on a portion of the outer surface of the intraluminal catheter that remains outside of the patient, wherein the antenna is configured to receive and/or transmit wireless data signals associated with the ultrasound imaging assembly while the antenna is positioned outside of the patient;

a second wireless communication hardware in communication with the first wireless communication hardware of the intraluminal imaging device via a wireless link; and an image processor in communication with the second wireless communication hardware, wherein the wireless data signals comprise echo data associated with ultrasound echo signals collected by the ultrasound imaging assembly for image generation at the image processor, wherein the first wireless communication hardware is configured to wirelessly transmit the wireless data signals to the second wireless communication hardware via the wireless link.

16. The wireless intraluminal imaging system of claim 15, further comprising a monitor in communication with the image processor, wherein the image processor generates an image based on the echo data, and wherein the monitor displays the image.

17. The wireless intraluminal imaging system of claim 15, wherein the wireless data signals comprise an instruction for controlling ultrasound signal generation at the ultrasound imaging assembly, and wherein the second wireless communication hardware wirelessly transmits the instruction to the first wireless communication hardware via the wireless link.

18. The wireless intraluminal imaging device of claim 1, wherein the ultrasound imaging assembly includes an ultrasound transducer array.

19. The wireless intraluminal imaging system of claim 15, wherein the ultrasound imaging assembly includes an ultrasound transducer array.

20. The wireless intraluminal imaging device of claim 1, wherein the proximal portion is configured to remain outside of a patient when the intraluminal catheter is positioned within the blood vessel such that the antenna is positioned outside of the patient and extends distally from the transceiver along the proximal portion of the intraluminal catheter.

21. The wireless intraluminal imaging system of claim 15, wherein the antenna extends distally from the transceiver along the proximal portion of the intraluminal catheter.

* * * * *